DS010624830B2

United States Patent
Deng et al.

(10) Patent No.: US 10,624,830 B2
(45) Date of Patent: Apr. 21, 2020

(54) AQUEOUS COMPOSITIONS WITH MANGIFERIN FOR COSMETIC APPLICATIONS

(71) Applicant: L'OREAL, Paris (FR)

(72) Inventors: Yang Deng, Green Brook, NJ (US); Zhi Pan, Ridgewood, NJ (US); Anne-Laure Suzanne Bernard, New York, NY (US); Shan Wu, Pudong New District Shanghai (CN)

(73) Assignee: L'OREAL, Paris (FR)

( * ) Notice: Subject to any disclaimer, the term of this patent is extended or adjusted under 35 U.S.C. 154(b) by 28 days.

(21) Appl. No.: 15/827,101

(22) Filed: Nov. 30, 2017

(65) Prior Publication Data
US 2019/0159989 A1     May 30, 2019

(51) Int. Cl.
| | | |
|---|---|---|
| *A61K 8/49* | (2006.01) | |
| *A61Q 17/00* | (2006.01) | |
| *A61Q 17/04* | (2006.01) | |
| *A61Q 19/08* | (2006.01) | |
| *A61K 8/73* | (2006.01) | |
| *A61K 8/06* | (2006.01) | |
| *A61K 8/67* | (2006.01) | |
| *A61K 8/60* | (2006.01) | |
| *A61K 8/81* | (2006.01) | |

(52) U.S. Cl.
CPC .............. *A61K 8/498* (2013.01); *A61K 8/062* (2013.01); *A61K 8/064* (2013.01); *A61K 8/4953* (2013.01); *A61K 8/602* (2013.01); *A61K 8/675* (2013.01); *A61K 8/731* (2013.01); *A61K 8/738* (2013.01); *A61K 8/8176* (2013.01); *A61Q 17/005* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 5,472,954 | A * | 12/1995 | Loftsson | A01N 25/10 514/58 |
| 5,824,320 | A | 10/1998 | Rouillard et al. | |
| 9,072,919 | B2 | 7/2015 | Pan et al. | |
| 9,107,853 | B2 | 8/2015 | Pan et al. | |
| 2002/0160040 | A1* | 10/2002 | Spicer | A61K 9/1274 424/451 |
| 2014/0107048 | A1* | 4/2014 | Pan | A61Q 19/00 514/27 |
| 2016/0051459 | A1 | 2/2016 | Perassinoto et al. | |
| 2017/0049758 | A1* | 2/2017 | Liang | A61K 47/02 |

FOREIGN PATENT DOCUMENTS

| | | |
|---|---|---|
| CN | 1977855 A | 6/2007 |
| CN | 101019877 A | 8/2007 |
| CN | 103462975 A | 12/2013 |
| CN | 103784356 A | 5/2014 |
| ES | 2464192 A1 | 5/2014 |
| WO | 2007124668 A1 | 11/2007 |
| WO | 2014059225 A1 | 4/2014 |
| WO | WO2014075866 A2 | 5/2014 |
| WO | 2014165471 A1 | 10/2014 |

OTHER PUBLICATIONS

U.S. Appl. No. 15/339,026, filed Oct. 31, 2016, US2018/0116936A1, Zhi Pan.
Anonymous, Moisturising Sun Milk SPF, MINTEL, Jun. 16, 2009, XP055552195, retrieved from www.gnpd.com, Database accession No. 1112925.
Anonymous, Dazzling Eye Cream, MINTEL, XP055552567, retrieved from www.gnpd.com, Database accession No. 1276487.
Anonymous, D-14 Shape Definer, MINTEL, Jun. 6, 2012, XP055552379, retrieved from www.gnpd.com, Database accession No. 1816033.
International Search Report for PCT/US2018/062162 dated Feb. 14, 2019.
Ling, et al., Standardised mangifera indica extract is an ideal antioxidant. Food Chemistry 113 (2009) 1154-1159. journal homepage: www.elsevier.com/locate/foodchem.
International Search Report for PCT/US2017/059273 dated Jan. 8, 2018.

* cited by examiner

*Primary Examiner* — Bong-Sook Baek
(74) *Attorney, Agent, or Firm* — McNees Wallace & Nurick LLC

(57) ABSTRACT

A cosmetic composition and a method of preparing a cosmetic composition that includes mangiferin characterized as demonstrating soluble and chemically stable mangiferin, wherein stability includes resistance to crystallization of mangiferin that is independent of temperature and pH.

14 Claims, No Drawings

AQUEOUS COMPOSITIONS WITH MANGIFERIN FOR COSMETIC APPLICATIONS

FIELD OF THE INVENTION

The present invention is generally directed to a cosmetic composition and a method for preparing the cosmetic composition that includes solubilized mangiferin. The composition is characterized as demonstrating soluble and stable mangiferin wherein stability includes resistance to crystallization of mangiferin that is independent of temperature or pH.

BACKGROUND OF THE INVENTION

The formation of free radicals is a widely accepted pivotal mechanism leading to skin aging. Free radicals are highly reactive molecules with unpaired electrons that can directly damage various cellular membranes, lipids, proteins, RNA and DNA. The damaging effects of these reactive oxygen species are induced internally during normal metabolism and externally through various oxidative stresses. UV exposure and environmental pollution can accelerate skin aging by producing free radicals in skin. Antioxidants protect cells from the damage of oxidative stress by scavenging free radicals and inhibiting following oxidation reactions. The topical application of antioxidants is broadly used in skin care products to prevent skin aging.

Mangiferin, a C-glucoside of tetrahydroxy-1,3,6,7 xanthone, is known to be an effective anti-microbial and anti-oxidant in which these activities are optimal below pH 5, and are diminished at pH that is greater than 7. In addition, the solubility of mangiferin in water and other common solvents for cosmetic applications is known to be adversely affected at lower temperatures (e.g., at 4° C.), and at pH that is less than 7. Hydrotropes such as niacinamide and caffeine have been used to enhance the solubility of mangiferin, but inclusion of hydrotropes does not provide any benefit with respect to its chemical stability, particularly in compositions having low pH (2-3), and in some compositions the level of hydrotrope needed for suitable solubility can have unwanted effects on the composition.

For the foregoing reasons, it is an object of the present invention to provide compositions in which mangiferin solubility and activity is preserved independent of temperature and pH.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In an exemplary embodiment, an aqueous cosmetic composition includes mangiferin, one or more of at least one hydrotrope and at least one cyclodextrin, and at least one polymeric precipitation inhibitor. The cosmetic composition is stable at any pH. In some embodiments, the composition includes at least one hydrotrope and at least one cyclodextrin.

In another exemplary embodiment, an aqueous cosmetic composition includes from about 0.01 to about 5.0 weight percent of mangiferin; from about 0.01 to about 25 weight percent of at least one hydrotrope or one cyclodextrin; from about 0.01 to about 25 weight percent of at least one polymeric precipitation inhibitor; and from about 0 to about 80 weight percent of solvent. The cosmetic composition is stable at any pH, in particular at a pH that is less than 7, including, for example, a pH of about 2-3. In some embodiments, the hydrotrope is selected from the group consisting of caffeine, vitamin B3 and combinations thereof.

In another exemplary embodiment, an aqueous cosmetic composition includes mangiferin, at least one hydrotrope or one cyclodextrin, at least one polymeric precipitation inhibitor, at least one cyclodextrin and at least one solvent. The cosmetic composition is stable at any pH.

In another exemplary embodiment, a method of preparing an aqueous cosmetic composition includes providing an isolate or extract comprising mangiferin up to 100% in purity mangiferin, and mixing the mangiferin with a polymeric precipitation inhibitor one or more of at least one hydrotrope and at least one cyclodextrin and at least one solvent to form a mixture, In some embodiments, the mangiferin is provided as an extract from mango leaf having a purity in the range from about 20 to about 100 weight percent. In some embodiments, the ingredients are mixed in any order. In some embodiments, the ingredients are mixed in a specific order. In some embodiments, the pH is adjusted after at least one addition of an ingredient to the mangiferin.

A further aspect of the invention provides methods for preparing a cosmetic formulation comprising an antioxidant composition, the method comprising the step of including in said formulation one or more components for forming one of an aqueous serum, an oil-in-water emulsion, and a water-in-silicone emulsion.

In one representative embodiment, a combination of hydrotropes, one or more of each of cyclodextrin and polymeric precipitation inhibitors are used to stabilize mangiferin in an acne treatment serum.

These and other aspects of the invention are set out in the appended claims, and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

"Cosmetically acceptable" means compatible with any keratinous substrate. For example, "cosmetically acceptable carrier" means a carrier that is compatible with any keratinous substrate.

"W/O emulsion," and "W/Si emulsion" as used herein, includes a water phase dispersed in an oil phase, where the oil phase is a continuous phase and includes at least one Si emulsifier.

The term "stable" as used herein refers to maintenance of mangiferin as solubilized in the solvent, wherein mangiferin is substantially not crystalized.

Applicants have surprisingly discovered that one or a combination of polymeric precipitation inhibitors with one or more of at least one hydrotrope and at least one cyclodextrin can prevent the crystallization of mangiferin and improve the stability of the composition, at one or both of low temperature and low pH, for example at pH less than 7, or less than 6, or less than 5, or less than 4, or less than 3, or less than 2. The compositions are characterized as demonstrating mangiferin chemical stability independent of pH.

In some embodiments, a cosmetic composition includes mangiferin, at least one hydrotrope, at least one polymeric precipitation inhibitor, and solvent, wherein the cosmetic composition is stable at any pH and at any hydrotrope dose.

In some embodiments, a cosmetic composition includes mangiferin, at least one cyclodextrin, at least one polymeric precipitation inhibitor, and solvent, wherein the cosmetic composition is stable at any pH and at any hydrotrope dose.

In some embodiments, a cosmetic composition includes from about 0.01 to about 5.0 weight percent of mangiferin; from about 0.01 to about 25 weight percent of at least one hydrotrope; from about 0.01 to about 25 weight percent of at least one polymeric precipitation inhibitor; and from about 0 to about 80 weight percent of solvent, wherein the cosmetic composition is stable at any pH and hydrotrope dose. In some embodiments, the hydrotrope is selected from the group consisting of caffeine, vitamin B3 and combinations thereof. In some embodiments, the composition further includes cyclodextrin.

In some embodiments, an aqueous cosmetic composition also includes one or more cyclodextrin, present in an amount from about 0.01 to about 25 weight percent.

In some embodiments, an aqueous cosmetic composition also includes one or more actives or other components, present in an amount from about 0.01 to about 50 weight percent.

Mangiferin

Mangiferin is a polyphenol with low solubility in water especially in cosmetic formulations, which are almost saturated with multiple actives. Mangiferin has poor solubility and stability, particularly at low temperatures, and at low pH. It has been shown that hydrotropes (including, caffeine, and niacinamide) aid in solubilizing polyphenols as described in U.S. Pat. No. 9,107,853; however, hydrotropes do not overcome solubility and stability problems both at pH greater than 7 and less than 7. Compositions according to the disclosure that employ mangiferin overcome these solubility and stability problems without reliance on high amounts of hydrotrope and independent of both temperature and pH.

Mangiferin as used in accordance with the disclosure is provided in an extract form. In some embodiments, mangiferin is provided as a mango leaf containing mangiferin in amounts from less than 50 weight percent and up to 99 weight percent or greater. More generally, other isolates and extracts can be obtained that contain mangiferin up to 100% in purity. Thus, it will be appreciated that the descriptor "an isolate or extract comprising mangiferin up to 100 weight percent in purity" means and includes, but is not limited to, mango leaf extract.

Thus, in accordance with the various embodiments, as used herein, mango leaf extract means and includes an extract consisting of about 100 weight percent mangiferin, as well as extracts comprising from less than about 50 weight percent mangiferin to up to about 99 weight percent mangiferin. In some representative examples, mango leaf extract may include mangiferin present at about 50 weight percent, or at about 70 weight percent, the remainder of the extract comprising other components. Thus, in the various embodiments as disclosed herein, the amount of mangiferin present in inventive compositions can be determined as the product of the weight percent of the mango leaf extract or other isolate or extract reagent used in the formulation and the percentage of mangiferin in the selected reagent. Thus, for example, inventive compositions comprising about 0.5 weight percent mango leaf extract prepared with a reagent that comprises about 70 weight percent mangiferin, would comprise about 0.35 weight percent mangiferin together with other components of the mango leaf extract. In some embodiments, mangiferin is provided having purity from less than about 50 weight percent, and in some embodiments from less than about 70 weight percent, and up to greater than about 99 weight percent, alone or together with other components, for example, in isolates or extracts from sources other than mango leaf. It will be appreciated that compositions according to the invention may comprise mango leaf extract or other isolates or extracts containing mangiferin. Thus, in another example, inventive compositions comprising one (1) weight percent of an isolate or other extract prepared with a reagent that comprises about 100 weight percent mangiferin, would comprise about one (1) weight percent mangiferin essentially free from other components in the isolate or extract.

The mangiferin present in the cosmetic composition, according to the disclosure, can be extracted from mango leaf. In some embodiments, the mangiferin is present in a given composition in an amount of from about 0.01 to about 5.0 weight percent, from about 0.1 to about 4 weight percent, from about 0.1 to about 3 weight percent, from about 0.1 to about 2 weight percent, and from about 0.1 to about 0.9 weight percent, from about 0.2 to about 0.8 weight percent, from about 0.3 to about 0.7 weight percent, from about 0.4 to about 0.6 weight percent or any suitable combination, sub-combination, range, or sub-range thereof. One of ordinary skill in the art, however, will appreciate that other ranges are within the scope of the invention.

Thus, the mangiferin is present by weight, based on the total weight of the composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0 to about 5.0 percent, including increments and ranges therein and there between.

Hydrotrope

In accordance with the disclosure, the composition includes one or more hydrotropes. In some embodiments, the composition includes two or more hydrotropes. In some embodiments, the at least one hydrotrope is present in an amount effective to increase transdermal penetration of mangiferin. At least one hydrotrope refers to one or a combination of two or more hydrotropes.

Most hydrotropes have aromatic structure with an ionic moiety, while some of them are linear alkyl chains, as listed below. Although hydrotropes noticeably resemble surfactants and have the ability to reduce surface tension, their small hydrophobic units and relatively shorter alkyl chain distinguish them as a separate class of amphiphiles. Consequently, their hydrophobicity is not sufficient enough to create well organized self-associated structures, such as micelles, even with a high concentration.

Common hydrotropic molecules include: sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethyl nicotinamide, N-picolylnicotinamide, N-allylnicotinamide, 2-methacryloyloxyethyl phosphorylcholine, resorcinol, butylurea, pyrogallol, N-picolylacetamide 3.5, procaine HCl, proline HCl, nicotinamide, pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Hydrotropes can be found in Lee J. et al., "Hydrotropic Solubilization of Paclitaxel: Analysis of Chemical Structures for Hydrotropic Property", Pharmaceutical Research, Vol. 20, No. 7, 2003; and Lee S. et al., "Hydrotropic Polymers: Synthesis and Characterization of Polymers Containing Picolylnicotinamide Moieties", Macromolecules, 36, 2248-2255, 2003.

Cosmetically acceptable hydrotropes refers to hydrotropes that can be used in cosmetic compositions. While hydrotropes represent a broad class of molecules used in various fields, cosmetic applications will be limited due to safety and tolerance restrictions. Suitable hydrotropes for use in cosmetics include, but are not limited to, vitamin B3, caffeine, sodium PCA (sodium salt of pyrrolidone carbonic acid), sodium salicylate, urea, and hydroxyethyl urea. The suitability of a hydrotrope for use in cosmetic compositions can be determined using tests known in the art for determining effects on skin, and toxicity to humans. Although these hydrotropes are given as an example, it will be appreciated that other hydrotropes compatible with cosmetic applications known in the art may be used. In some embodiments, the vitamin B3 may include niacinamide, nicotinic acid, nicotinyl alcohol, esters or salts thereof, or combinations thereof.

In accordance with the various embodiments, the amount of hydrotrope present in the composition can range from about 0.01 to about 25 weight percent; from about 0.01 to about 20 weight percent; or from about 0.01 to about 10 weight percent, based on the total weight of the composition. In some embodiments, the hydrotrope is present in a given composition in an amount of from about 1.0 to about 1.5 weight percent, from about 1.1 to about 1.4 weight percent, from about 1.2 to about 1.3 weight percent, or any suitable combination, sub-combination, range, or sub-range thereof. In some embodiments according to the disclosure, from about 0.01 weight percent or more hydrotrope may be used in a combination with mangiferin, cyclodextrin and solvent. In some embodiments according to the disclosure, not more than about 5 weight percent, or not more than about 3 weight percent, or not more than about 1.5 weight percent hydrotrope may be used in a combination with mangiferin, cyclodextrin and solvent. In some embodiments, two or more hydrotropes are present. One of ordinary skill in the art, however, will appreciate that other ranges are within the scope of the invention.

Thus, one or of a combination, such as two or three, hydrotropes may be present by weight, based on the total weight of the composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24 to about 25 weight percent, including increments and ranges therein and there between.

Polymeric Precipitation Inhibitors (PPI)

In accordance with the disclosure, the composition includes one or more polymeric precipitation inhibitors. In some embodiments, the composition includes two or more polymeric precipitation inhibitors. In some embodiments, the at least one polymeric precipitation inhibitor is present in an amount effective to stabilize active ingredients in the composition.

Polymeric precipitation inhibitors (PPI) that are present in the cosmetic composition, according to the various embodiments, include, but are not limited to, hydroxypropyl methylcellulose (HPMC), hydroxypropyl cellulose (HPC), polyvinylpyrrolidone (PVP), or combinations thereof. Although these polymeric precipitation inhibitors are given as an example, it will be appreciated that other polymeric precipitations compatible with cosmetic applications known in the art may be used. In some embodiments, the at least one polymeric precipitation inhibitor in combination with cyclodextrin show synergistic effects in terms of stability. Good results have been obtained with HPMC and cyclodextrin in the absence of hydrotrope, and with PVP or HPC and a hydrotrope in the absence of cyclodextrin.

In accordance with the various embodiments, polymeric precipitation inhibitors are present in a given composition in an amount of from about 0.01 to about 25 weight percent, based on the total weight of the composition. In some embodiments, polymeric precipitation inhibitors are present in an amount from about 0.01 to about 15 weight percent, or from about 0.01 to about 10 weight percent, or from about 0.01 to about 5 weight percent. In some embodiments, polymeric precipitation inhibitors are present in a given composition in an amount of from about 0.01 to about 25 weight percent, from about 5 to about 20 weight percent, from about 10 to about 15 weight percent, from about 15 to about 20 weight percent, from about 20 to about 25 weight percent or any suitable combination, sub-combination, range, or sub-range thereof.

In some embodiments, polymeric precipitation inhibitors that are present in the cosmetic composition has an average molecular weight between 1,000 g/mol and 9,000,000 g/mol. In some embodiments, HPC or HPMC has a molecular weight from about at least 340,000 up to about 9 MM, or up to about 2 MM. In some embodiments, a PPI has a molecular weight that is equal to or greater than about 340,000, or about 400,000, or about 500,000, or about 750,000 or about 850,000, or about 1 MM.

According to the embodiments of the disclosure, good results have been obtained using higher molecular weight PPIs in amounts of about 2 percent by weight based upon the total weight of the composition. In general, higher molecular weight PPIs demonstrated enhanced capability to stabilize mangiferin solubility and chemical activity. For Example, compositions including HPC with a molecular weight of about 850,000 demonstrate enhanced mangiferin stabilization in comparison with compositions including HPC with a molecular weight of about 80,000. Similarly, compositions including PVP with a molecular weight in the range from about 360,000 to about 2,550,000 demonstrate enhanced mangiferin stabilization in comparison with compositions including mangiferin with a molecular weight in the range from about 4,500 to about 200,000. And in some examples, compositions including HMPC with a molecular weight from about 340,000 and present at about 0.5 percent by weight based upon the total weight of the composition demonstrate enhanced mangiferin stabilization, and even greater stabilization when combined with beta-cyclodextrin (BCD) at about 0.5 percent by weight based upon the total weight of the composition.

Thus, one or a combination, such as two or three, polymeric precipitation inhibitors may be present, by weight, based on the total weight of the composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20 to about 25 percent, including increments and ranges therein and there between.

Cyclodextrin

In accordance with some embodiments, one or more cyclodextrin may be present in the composition. Cyclodextrins are cyclic oligosaccharides. Cyclodextrin that is present in the cosmetic composition, according to the various embodiments, includes, but is not limited to, alpha-cyclodextrin (ACD), beta-cyclodextrin (BCD), gamma-cyclodextrin (GCD), hydroxypropyl-beta-cyclodextrin (HPACD), hydroxypropyl-gamma-cyclodextrin (HPGCD) and combinations thereof. Although these cyclodextrins are given as an example, it will be appreciated that other cyclodextrins compatible with cosmetic applications known in the art may be used.

In accordance with some embodiments, cyclodextrin is present in a given composition in an amount of from about 0.01 to about 25 weight percent, from about 0.01 to about 20 weight percent, from about 0.01 to about 10 weight percent based on the total weight of the composition. In some embodiments, cyclodextrin, when present, is present in an amount from at least about 0.01 weight percent, from at least 0.25 weight percent, or from at least about 0.5 weight percent. In some embodiments, cyclodextrin is present in a given composition in an amount of from about 0.05 to about 2.5 weight percent, from about 0.05 to about 0.5 weight percent, from about 0.05 to about 1 weight percent, from about 0.05 to about 1.5 weight percent, from about 0.05 to about 2.0 weight percent, from about 0.05 to about 2.5 weight percent. In some embodiments, cyclodextrin is present from about 0.1 to about 1.0 weight percent, from about 0.2 to about 2.4 weight percent, from about 0.3 to about 2.3 weight percent, from about 0.4 to about 2.2 weight percent, from about 0.5 to about 2.1 weight percent, from about 0.6 to about 2.0 weight percent, from about 0.7 to about 1.9 weight percent, from about 0.8 to about 1.8 weight percent, from about 0.9 to about 1.7 weight percent, from about 1.0 to about 1.6 weight percent, from about 1.1 to about 1.5 weight percent, from about 1.2 to about 1.4 weight percent, or any suitable combination, sub-combination, range, or sub-range thereof. In some embodiments, two or more cyclodextrins are present. One of ordinary skill in the art, however, will appreciate that other ranges are within the scope of the invention.

Thus, one or a combination, such as two or three, cyclodextrins may be present, by weight, based on the total weight of the composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20 to about 25 weight percent, including increments and ranges therein and there between.

Solvent

In accordance with the disclosure, one more solvent is present in the composition. The solvent present in the cosmetic composition, according to the disclosure, includes, but is not limited to, alcohol, propylene glycol, water or combinations thereof. Although these solvents are given as an example, it will be appreciated that other solvents compatible with cosmetic applications known in the art may be used.

In accordance with the various embodiments, solvent is present in a given composition in an amount of from about 0 to about 90 weight percent, based on the total weight of the composition. In some embodiments, solvent is present in a given composition in an amount from about 0 to about 80 weight percent, from about 10 to about 70 weight percent, from about 20 to about 60 weight percent, of from about 30 to about 50 weight percent or any suitable combination, sub-combination, range, or sub-range thereof. One of ordinary skill in the art, however, will appreciate that other ranges are within the scope of the invention.

Thus, the one or combination of solvents may be present by weight, based on the total weight of the composition, from about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, to about 90 weight percent, including increments and ranges therein and there between.

Water

The compositions comprise from about 1 to about 90 weight percent of water, with respect to the total weight of the composition. The amount of water in the composition can range from about 1 to 90 weight percent; from about 1 to 60 weight percent; or from about 1 to 50 weight percent, based on the total weight of the composition.

The pH of the composition is not limited but is generally between 2 and 12, and in some embodiments is one of between 3 and 11, and between 5 and 9, and between 6 and 8, and 7. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Optional Components

In some embodiments, there may be one or more actives present in the cosmetic composition, according to the disclosure, the active selected from, for example, humectants, such as acetamide MEA, glycols, such as glycerin and propylene glycol; alcohol; anti-microbial components such as zinc pyrrolidone carboxylic acid (zinc PCA); caprylyl glycol; salicylic acid, alpha hydroxy acid; anti-oxidant compounds, including, phenolic compounds, such as chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenol s, betacyanins, capsaicinoids, hydroxybenzoketones, methoxyphenols, naphthoquinones, and phenolic terpenes, resveratrol, curcumin, pinoresinol, ferulic acid, hydroxytyrosol, cinnamic acid, caffeic acid, p-coumaric acid, baicalin (Scutellaria baicalensis root extract), pine bark extract (Pinus pinaster bark/bud extract), ellagic acid; and vitamins and vitamin derivatives, such as panthenol, tocopherol and other Vitamin E derivatives, ascorbic acid; and combinations thereof.

In some embodiments, there may be one or more other components present in the cosmetic composition, according to the disclosure, the additives selected from, preservatives, such as phenoxyethanol; surfactants, including silicone surfactants, W/O and O/W surfactants; oils, including cosmetic oils, fatty compounds, silicone oils such as dimethicone, botanical oils and essential oils; emulsifiers, including silicone emulsifiers; elastomers; fillers such as clays, talc, organic thickeners with for instance, anionic, cationic, non-ionic, and amphoteric polymeric associative thickeners and combinations thereof; carbomers; polymers; penetrants;

sequestrants; fragrances; dispersants; film-forming agents; ceramides; opacifiers and combinations thereof.

Although the aforementioned optional components are given as an example, it will be appreciated that other optional components compatible with cosmetic applications known in the art may be used.

In accordance with the various embodiments, amounts of optional components present in the composition can range from about 0 to about 50 weight percent, from about 0.5 to about 30 weight percent, from about 1.5 to about 20 weight percent, and from about 5.0 to about 15 weight percent.

In some embodiments, one or more actives, alone or in combination, each can be present in the composition according to the disclosure from about 0.05 to about 50 weight percent, from about 0.05 to about 2.5 weight percent, from about 0.1 to about 2.0 weight percent, from about 0.25 to about 1.5 weight percent, and from about 0.5 to about 1.25 weight percent.

In some embodiments, one or more other components, such as vitamins, preservatives, and the like, alone or in combination, each can be present in the composition according to the disclosure from about 0.05 to about 50 weight percent, from about 0.05 to about 25 weight percent, from about 0.1 to about 10 weight percent, from about 0.25 to about 5.0 weight percent, and from about 0.5 to about 3.5 weight percent. The following examples are intended to further illustrate the present invention. They are not intended to limit the invention in any way. Unless otherwise indicated, all parts are by weight.

Thus, the one or combination of optional components may be present by weight, based on the total weight of the composition, from about 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 25, 30, 35, 40, 45 to about 50 weight percent, including increments and ranges therein and there between.

The following examples are intended to further illustrate the present invention. They are not intended to limit the invention in any way. Unless otherwise indicated, all parts are by weight.

In one representative example, a formulation may be prepared containing a combination of at least one of a hydrotrope and a cyclodextrin, together with mangiferin, water, a mixture of actives including one or more of zinc PCA, ferulic acid, ascorbic acid, salicylic acid, and additives that include propylene glycol, panthenol, denatured alcohol. In some embodiments the hydrotrope is selected from caffeine, niacinamide, and mixtures thereof.

In another representative example, a serum formulation may be prepared containing a combination of at least one of a hydrotrope and a cyclodextrin, together with mangiferin, water, a mixture of actives and additives that include propylene glycol, panthenol, denatured alcohol. In some embodiments the hydrotrope is selected from caffeine, niacinamide, and mixtures thereof.

In yet another representative example, a water in oil emulsion, such as a rich melting cream formulation may be prepared containing a combination of at least one of a hydrotrope and a cyclodextrin, together with mangiferin, water, a mixture of actives and additives that include chelating agents, pH adjusters, sodium chloride, oil phase components including cosmetic oils, fatty compounds, silicones and silicone emulsifiers, surfactants, dimethicone, and water phase components including surfactants, glycerin, water, and alcohol, and also including preservatives such as phenoxyethanol, caprylyl glycol, vitamins such as tocopherol, polymers and fillers. In some embodiments the hydrotrope is selected from caffeine, niacinamide, and mixtures thereof.

In yet another representative example, an oil in water emulsion formulation may be prepared containing a combination of at least one of a hydrotrope and a cyclodextrin, together with mangiferin, water, a mixture of actives and additives that include oil phase components including cosmetic oils, fatty compounds, surfactants, glycerin, water, preservatives caprylyl glycol, carbomers and polymers. In some embodiments the hydrotrope is selected from caffeine, niacinamide, and mixtures thereof.

EXAMPLES

Representative examples of inventive compositions are shown in Table 1, and inventive compositions component ranges are shown in Table 2. Inventive compositions may be prepared according to methods consistent with those described herein and may be subjected to stability evaluation at temperatures that range from and include 4° C., 25° C. and 45° C.

TABLE 1A

Inventive cosmetic compositions (components shown as percentages based on the total weight of the composition)

| Component | Inventive 1 | Inventive 2 | Inventive 3 | Inventive 4 | Inventive 5 | Inventive 6 |
|---|---|---|---|---|---|---|
| Hydrotrope | 1.25 | 1.25 | 1.25 | 1.25 | 1.25 | |
| *Mangifera Indica* (Mango) Leaf Extract | 0.5 | 0.5 | 0.5 | 0.5 | 0.5 | 0.5 |
| HPMC | | | | 0.5 (340,000 MW) | 0.5 (340,000 MW) | 0.5 (340,000 MW) |
| HPC | | | 0.25 (850,000 Mw) | | | |
| PVP | 2 (360,000 MW) | 2 (360,000 MW) | | | | |
| Cyclodextrin | | 1 (BCD) | | | 0.5 (BCD) | 0.5 (HPGCD) |
| Alcohol | 25 | 25 | 25 | 25 | 25 | 25 |
| Water | 48.5 | 47.5 | 50.25 | 50 | 49.5 | 50.75 |
| Actives | 12 | 12 | 12 | 12 | 12 | 12 |
| Humectant | 7.5 | 7.5 | 7.5 | 7.5 | 7.5 | 7.5 |
| Vitamin | 3.75 | 3.75 | 3.75 | 3.75 | 3.75 | 3.75 |
| Ph | ~3 | ~3 | ~3 | ~3 | ~3 | ~3 |
| Stability At 4° C. (>/=8 Weeks) | N | N | Y | N | Y | Y |

TABLE 1B

Inventive cosmetic compositions (components shown as percentages based on the total weight of the composition)

| Component | Inventive 7 Serum | Inventive 8 W/O emulsion | Inventive 9 O/W emulsion | Inventive Ranges/MW |
|---|---|---|---|---|
| Hydrotrope | 1.25 | 2 | | 0.01-10 |
| Mangifera Indica (Mango) Leaf Extract | 0.5 | 0.5 | 0.5 | 0.01-1 |
| HPMC | 0.5 | 0.5 | 0.5 | PPI |
| HPC | | | | 0.01-25 |
| PVP | | | | 300,000-9,000,000 MW |
| Cyclodextrin | 0.5 | 0.5 | 2 | 0.01-25 ACD, BCD, GCD, HPACD, HPBCD and HPGCD |
| Alcohols | 25 | | | 0-50 |
| Water | 49.5 | 51.55 | 63.7 | 25-95 |
| Actives | 12 | 0.15 | | 0-50 |
| Humectants | 7.5 | 3 | 5 | 0-50 |
| Vitamins | 3.75 | 1 | 3.75 | 0-50 |
| Additives/ Preservatives | | 1.8 | 1.0 | 0-50 |
| Oils | | 26 | 17 | 0-50 |
| Polymers/ Thickeners | | 2 | 5.3 | 0-50 |
| Surfactants/ Emulsifiers | | 13 | 5 | 0-50 |
| Ph | </=3 | NA | ~5 | |
| Stability At 4° C. (>/=8 Weeks) | Y | Y | Y | |

Representative examples of comparative compositions are shown in Table 2.

TABLE 2

Comparative cosmetic compositions.

| Component | Comparative 1 | Comparative 2 | Comparative 3 | Comparative 4 |
|---|---|---|---|---|
| Hydrotrope | | | 1.25 | 1.25 |
| Mangifera Indica (Mango) Leaf Extract | 0.5 | 0.5 | 0.5 | 0.5 |
| Cyclodextrin (BCD) | | 0.5 | | 0.5 |
| Alcohols | 25 | 25 | 25 | 25 |
| Water | 51.75 | 51.25 | 50.5 | 50 |
| Actives | 12 | 12 | 12 | 12 |
| Humectants | 7.5 | 7.5 | 7.5 | 7.5 |
| Vitamins | 3.75 | 3.75 | 3.75 | 3.75 |
| Stability At 4° C. (Week) | N | N | N | N |

In one representative embodiment of making compositions in accordance with the disclosure, the following procedure describes the process by which Inventive Examples (1-6) and Comparative Examples were prepared, generally. Specific examples for some compositions are further described below. All ingredients except hydroxypropyl cellulose and hydroxypropyl methylcellulose, can be dissolved first with heat under low shear. After the solution becomes clear, the hydroxypropyl cellulose or hydroxypropyl methylcellulose can be added directly to the heated mixture or first dispersed in the glycol (propylene glycol or glycerin) and then added to mixture. The mixture is subjected to low homogenization until all hydroxypropyl cellulose or hydroxypropyl methylcellulose is dissolved. At room temperature, alcohol soluble ingredients can be dissolved in alcohol and then the alcohol solution can be blended into the mixture. The combined mixtures can be blended with low shear until the solution becomes clear.

Representative cosmetic serum and emulsion compositions are shown in Table 1B.

Referring to Table 1A, Inventive Example 6 is a composition having a pH less than 3. Preparation of the composition includes the process including the steps of: (1) adding mangiferin to water; (2) adjusting the pH to at least 8 and letting stand for ~1 min or until the solution is clear; (3) adding cyclodextrin to the solution, and after dissolved, adjusting the pH to below 7; (4) adding PPI either directly to the water phase or first to the humectant (for example, propylene glycol or glycerin) and then combining into the water phase to disperse well; and (5) combining alcohol-soluble components with alcohol then combining with the mangiferin/PPI/cyclodextrin mixture.

Referring to Table 1B, Inventive Example 7 is a serum formulation having a pH of approximately 3, and includes components as listed. Preparation of the serum includes the process including the steps of: (1) providing an isolate or extract comprising mangiferin up to 100% in purity mangiferin; (2) mixing caffeine with water to form a mixture; (3) adding the mangiferin into the mixture; (4) adding cyclodextrin, and stirring until it is dissolve completely; (5) adding HPMC to the mixture of the mangiferin; (6) adding other solvent and actives and other additives, heating if need, then adding alcohol at the last step in low temperature.

In another example the composition is formed in a batch process.

Referring again to Table 1B, Inventive Example 8 is a water in oil (W/O) emulsion formulation (pH not determined), and includes components as listed. Preparation of the W/O emulsion includes the process including the steps of: (1) adding niacinamide, caffeine and mangiferin to water; (2) heating the water phase to 60 degrees C.; (3) adding cyclodextrin followed by HPMC to the water phase one by one, to disperse well; (5) separately heating the oil phase to 80 degrees C.; (6) adding the water phase to the oil phase, then homogenizing for 10 min to form an emulsion; (7) adding the polymer to the emulsion to disperse; (8) cooling the mixture, then adding dimethicone and tocopherol.

In another example the O/W emulsion composition is formed in a batch process.

Referring again to Table 1B, Inventive Example 9 is an oil in water (O/W) emulsion formulation (pH ~5), and includes components as listed. Preparation of the O/W emulsion includes the process including the steps of: (1) adding mangiferin to water; (2) adjusting the pH to 10~10.5 and letting stand for ~1 min; (3) adding Hydroxypropyl Cyclodextrin to solution, and after dissolved, adjusting the pH to 5.6~5.8; (4) adding Hydroxypropyl Methylcellulose to the water phase to disperse well; (5) heating water phase and oil phase to 80 degree C.; (6) adding oil phase to water phase, and homogenizing for 10 min; (7) adding polymer into emulsion and mixing to disperse; (8) cooling.

The stability of each composition was measured after preparation. Samples were subjected to conditions of 4° C. and evaluated weekly to assess whether they show the sign of any undesirable crystallization which would indicate instability. Compositions showing stability for up to or more than 8 weeks are considered to pass (with reference to Tables 1 and 2, stability is indicated as Y and instability as N).

The comparative examples 1-4 in Table 2 were prepared in a similar manner to inventive examples 1-5, except that the comparative examples lack one or more of hydrotropes, polymeric precipitation inhibitors and PPI/cyclodextrin.

Comparative examples 1-4 show lower stability than inventive examples 1-5. Based on the results of performance of inventive vs. comparative compositions, hydrotropes with PPI or a combination of PPI and cyclodextrin significantly improve the physical stability of mangiferin in cosmetic formulations. Further, Inventive Example 7 having both a polymeric precipitation inhibitor and cyclodextrin, for example, shows synergistic effects in terms of stability, compared to the compositions of Comparative Example 4 and Inventive Example 4.

TABLE 3

| Results | | | | |
|---|---|---|---|---|
| SAMPLE | HYDRO-TROPE | PPI | CYCLO-DEXTRIN | PH | PASS STABILITY |
| Inventive 1 | YES | YES | NO | ~3 | NO |
| Inventive 2 | YES | YES | YES | ~3 | NO |
| Inventive 3 | YES | YES | NO | ~3 | YES |
| Inventive 4 | YES | YES | NO | ~3 | NO |
| Inventive 5 | YES | YES | YES | ~3 | YES |
| Inventive 6 | NO | YES | YES | ~3 | YES |
| Inventive 7 | YES | YES | YES | ~3 | YES |
| Inventive 8 | YES | YES | YES | NA | YES |
| Inventive 9 | NO | YES | YES | ~5 | YES |
| Comparative 1 | NO | NO | YES | ~3 | NO |
| Comparative 2 | NO | NO | YES | ~3 | NO |
| Comparative 3 | YES | NO | NO | ~3 | NO |
| Comparative 4 | YES | NO | YES | ~3 | NO |

Referring to Table 3, it is evident that mangiferin stability, which according to the disclosure is maintenance of mangiferin solubility without crystallization over time when maintained at 4° C., is independent of pH and can be maintained without high amounts of hydrotrope, and, at low pH, even in the absence of hydrotrope (see Inventive examples 6 and 9) despite its known low solubility at low pH and without high amounts of hydrotrope. Further, the results show that compositions that include at least one of a hydrotrope or cyclodextrin with a PPI provide stability. And as shown with the comparative compositions, cyclodextrin and hydrotrope, alone or in combination, are not sufficient to provide mangiferin stability.

Compositions and formulations as described in the representative embodiments herein are selected from commercially available materials, including, for example: one of Mango Leaf Extract with from less than 50 weight percent and up to 100 weight percent mangiferin.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, "weight percent" of an active in a composition is represented as the amount of raw material containing the active that is used, and may or may not reflect the final percentage of the active, wherein the final percentage of the active is dependent on the weight percent of the active in the raw material.

All ranges and amounts given herein are intended to include subranges and amounts using any disclosed point as an end point. Thus, a range of "1 to 10 weight percent, such as 2 to 8 weight percent, such as 3 to 5 weight percent," is intended to encompass ranges of "1 to 8 weight percent," "1 to 5 weight percent," "2 to 10 weight percent," and so on. Other than in the operating examples, or where otherwise indicated, all numbers, amounts, ranges, etc., are intended to be modified by the term "about," whether or not so expressly stated. Similarly, a range given of "about 1 to 10 weight percent" is intended to have the term "about" modifying both the 1 and the 10 weight percent endpoints, meaning within 10 weight percent of the indicated number (e.g. "about 10 weight percent" means 9-11 weight percent and "about 2 weight percent" means 1.8-2.2 weight percent). Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made, and equivalents may be substituted for elements thereof without departing from the scope of the invention. In addition, many modifications may be made to adapt a particular material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cosmetic composition comprising:
   a. mangiferin;
   b. at least one hydrotrope selected from caffeine, vitamin B3 and combinations thereof;
   c. at least one polymeric precipitation inhibitor selected from hydroxypropyl methylcellulose, hydroxypropyl cellulose, and combinations thereof;
   d. at least one cyclodextrin selected from alpha-cyclodextrin, beta-cyclodextrin, gamma-cyclodextrin, hydroxypropyl-beta-cyclodextrin, hydroxypropyl-gamma-cyclodextrin, other cyclodextrin derivatives and combinations thereof; and
   e. solvent;
   wherein the cosmetic composition has a pH that is at or below pH 5 and wherein the cosmetic composition demonstrates stability against crystallization of mangiferin at 4° C. at a pH that is less than 5.

2. The composition of claim 1, wherein the mangiferin is employed in an amount of from about 0.01 to about 5.0% by weight, based on the total weight of the composition.

3. The composition of claim 1, wherein the at least one of at least one hydrotrope and at least one cyclodextrin is employed in an amount of from about 0.01 to about 25% by weight, based on the total weight of the composition.

4. The composition of claim 1, wherein the polymeric precipitation inhibitor is employed in an amount of from about 0.01 to about 25% by weight, based on the total weight of the composition.

5. The composition of claim 1, wherein the solvent is employed in an amount of from about 0 to about 90% by weight, based on the total weight of the composition.

6. The composition of claim 1, wherein the vitamin B3 is selected from niacinamide, nicotinic acid, nicotinoyl alcohol; esters or salts thereof and combinations thereof.

7. The composition of claim 1, wherein the solvent is selected from denatured alcohol, propylene glycol, water and combinations thereof.

8. The composition of claim 1, further comprising one or more additional components selected from a humectant, antimicrobial, antioxidant, preservative, vitamin, vitamin derivative; and a filler, thickener, penetrant, fragrance, dispersant, film-forming agent; ceramide; opacifier and combinations thereof.

9. The composition of claim 8, further comprising one or more components selected from acetamide MEA, glycol, glycerin, propylene glycol; alcohol; zinc pyrrolidone carboxylic acid, salicylic acid, alpha hydroxy acid; phenolic compounds, chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, phenolic terpenes, resveratrol, curcumin, pinoresinol, ferulic acid, hydroxytyrosol, cinnamic acid, caffeic acid, p-coumaric acid, baicalin (Scutellaria Baicalensis root extract), pine bark extract (Pinus Pinaster bark/bud extract), ellagic acid; and vitamins, vitamin derivatives panthenol, ascorbic acid and combinations thereof.

10. An aqueous cosmetic composition comprising:
   a. from about 0.01 to about 5.0 weight percent of mangiferin;
   b. from about 0.01 to about 25 weight percent of at least one hydrotrope selected from caffeine, vitamin B3 and combinations thereof;
   c. from about 0.01 to about 10 weight percent of at least one cyclodextrin selected from alpha-cyclodextrin, beta-cyclodextrin, gamma-cyclodextrin, hydroxypropyl-beta-cyclodextrin, hydroxypropyl-gamma-cyclodextrin, other cyclodextrin derivatives and combinations thereof;
   d. from about 0.01 to about 25 weight percent of at least one polymeric precipitation inhibitor selected from hydroxypropyl methylcellulose, hydroxypropyl cellulose, and combinations thereof; and
   e. from about 0 to about 90 weight percent of solvent;
   wherein the cosmetic composition has a pH that is at or below pH 5 and wherein the cosmetic composition demonstrates stability against crystallization of mangiferin at 4° C. at a pH that is less than 5.

11. A method of preparing a cosmetic composition of claim 1, comprising:
   a. providing an isolate or extract comprising mangiferin up to 100% in purity mangiferin;
   b. providing at least one hydrotrope selected from caffeine, vitamin B3 and combinations thereof, at least one cyclodextrin selected from alpha-cyclodextrin, beta-cyclodextrin, gamma-cyclodextrin, hydroxypropyl-beta-cyclodextrin, hydroxypropyl-gamma-cyclodextrin, other cyclodextrin derivatives and combinations thereof, and at least one polymeric precipitation inhibitor selected from hydroxypropyl methylcellulose, hydroxypropyl cellulose, and combinations thereof;
   c. mixing the mangiferin, the at least one hydrotrope, and at least one solvent to form a mixture;
   d. adding the at least one polymeric precipitation inhibitor to the mixture; and
   e. adding the at least one cyclodextrin to the mixture.

12. A method of preparing a cosmetic composition according to claim 1 comprising:
   a. providing an isolate or extract comprising mangiferin up to 100% in purity mangiferin;

b. providing at least one hydrotrope selected from caffeine, vitamin B3 and combinations thereof, at least one cyclodextrin selected from alpha-cyclodextrin, beta-cyclodextrin, gamma-cyclodextrin, hydroxypropyl-beta-cyclodextrin, hydroxypropyl-gamma-cyclodextrin, other cyclodextrin derivatives and combinations thereof, and at least one polymeric precipitation inhibitor selected from hydroxypropyl methylcellulose, hydroxypropyl cellulose, and combinations thereof;

c. mixing the mangiferin, the at least one hydrotrope, and at least one solvent to form a mixture;

d. adjusting the pH to above 7 to dissolve the mangiferin;

e. adding the at least one cyclodextrin to the mixture;

f. adjusting the pH to below 7; and g. adding the at least one polymeric precipitation inhibitor to the mixture.

13. The cosmetic composition of claim 1, wherein the at least one polymeric precipitation inhibitor is hydroxypropyl methylcellulose.

14. The cosmetic composition of claim 13, wherein the composition demonstrates stability against crystallization of mangiferin at 4° C. at a pH that is less than 3.

* * * * *